United States Patent
Arcamone et al.

[11] Patent Number: 6,150,325
[45] Date of Patent: Nov. 21, 2000

[54] BICYCLIC TACHYKININS ANTAGONISTS, PREPARATION THEREOF AND THEIR USE IN PHARMACEUTICAL COMPOSITIONS

[75] Inventors: Federico Arcamone, Nerviano; Carlo Alberto Maggi, Florence; Laura Quartara, Campi Bisenzio; Danilo Giannotti, Altopascio, all of Italy

[73] Assignee: A. Menarini Industrie Farmaceutiche Riunite S.r.l., Florence, Italy

[21] Appl. No.: 08/929,215

[22] Filed: Sep. 9, 1997

[30] Foreign Application Priority Data

Mar. 13, 1995 [IT] Italy .................. FI95 A 0044

[51] Int. Cl.[7] ............... A01N 61/00; C07K 14/00; C07K 16/00; C07K 17/00
[52] U.S. Cl. ............... 514/1; 530/300; 530/333; 530/317; 530/322; 530/323; 530/329; 530/330; 536/22.1; 536/23.1
[58] Field of Search ................ 514/1; 530/300, 530/333, 317, 322, 323, 329, 330; 536/22.1, 23.1

[56] References Cited

FOREIGN PATENT DOCUMENTS

WO 9321227   10/1993   WIPO .

OTHER PUBLICATIONS

Holzemann et al., Int. J. Peptide & Protein Res. (1994) 44, 105–111.

*Primary Examiner*—Jezia Riley
*Attorney, Agent, or Firm*—Hedman, Gibson & Costigan, P.C.

[57] ABSTRACT

This invention relates to novel compounds of general formula (I):

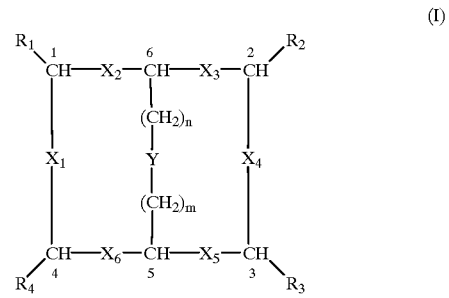

and to pharmaceutical compositions containing them.

14 Claims, No Drawings

BICYCLIC TACHYKININS ANTAGONISTS, PREPARATION THEREOF AND THEIR USE IN PHARMACEUTICAL COMPOSITIONS

FIELD OF THE INVENTION

This invention relates to novel bi-cyclic compounds useful in pharmaceutical compositions as tachykinins antagonists, and to pharmaceutical compositions containing them.

BACKGROUND OF THE INVENTION

The receptor $NK_2$ of tachykinins is widely expressed in the peripheral nervous system of Mammalia. One of the several effects caused by the selective stimulation of the receptor $NK_2$ is the contraction of the smooth muscles. Therefore, antagonists of the receptor $NK_2$ can be considered agents able to control the hypercontraction of the smooth muscles in any patological condition in which the release of the tachykinins contributes to the rise of the corrispondent disorder. In particular, the bronchospastic component of asthma, cough, pulmonary irritations and local spasms of the urinary bladder and of the ureter during cystitis, infections and renal colics can be considered conditions in which the administration of receptor $NK_2$ antagonists can be effective (A. L. Magnan et al. *Neuropeptides*, 1993, 24, 199). Compounds which act as antagonists of the tachykinins, and in particular of the neurokinin A, are well-known in Literature. Among them, the cyclic compounds (B. J. Williams et al. *J. Med. Chem.*, 1993, 36, 2) are of particular interest. Lipophily has been defined as an essential requirement in order to have an intensive antagonist activity to the receptor $NK_2$ of the tachykinins of a series of cyclic pseudopeptides (L. Quartara et al. *J. Med. Chem.*, 1994, 27) and particularly in case of bicyclic hexapeptides. WO/93/21227). Surprisingly it has been now found that products structurally similar to those described above, but in which, however, at least one hydrophilic group is present, not only keep their high affinity in vitro, but also show an increase in the pharmacological activity in vivo if compared to the corrispondent compounds which do not contain any hydrophilic group.

This is even more surprising if it is taken into account that monocyclic peptides having antagonist properties which are similar to those of the tachykinins do not show any increase in the pharmacological activity when hydrophilic groups are introduced onto the structure of the cycle [Int. J. Peptide Protein Res. (1984), 44:2, 105–111].

SUMMARY

This invention relates to novel compounds of the general formula (I):

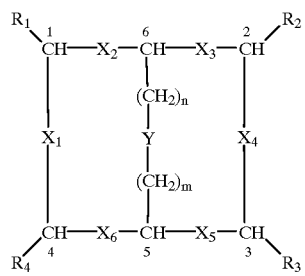

wherein:

$X_1$, $X_2$, $X_3$, $X_4$, $X_5$, and $X_6$, same or different from one another, represent a —NR'CO— or a —CONR'— group, wherein R' is H or $C_{1-3}$ alkyl;

Y represents a group selected from —NRCO—, —CONR—, or —SS— wherein R is H or $C_{1-3}$ alkyl;

at least one of the $R_1$, $R_2$, $R_3$ and $R_4$ groups, same or different from one another, is hydrophilic and the remaining groups are hydrophobic;

m and n, same or different from one another, are each an integer number from 1 to 4;

and to pharmaceutical compositions containing them.

DETAILED DESCRIPTION OF THE INVENTION

The present invention relates to novel compounds having the general formula (I)

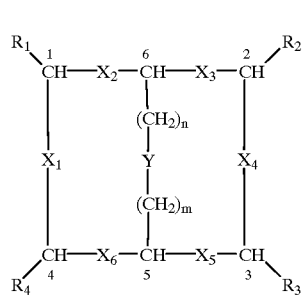

wherein $X_1$, $X_2$, $X_3$, $X_4$, $X_5$, $X_6$; Y, $R_1$, $R_2$, $R_3$, $R_4$, m and n groups are as defined above;

processes for the preparation thereof and pharmaceutical compositions containing them.

The formula (I) as reported above is considered the one giving the best representation of the real spatial structure of the bicyclic peptide according to the invention. However also the following Formula (Ia) (which chemically speaking is identical to Formula (I)) is given in order to simplify the understanding of the compounds described hereinafter and in the Examples with their chemical name in particular in so far as the groups $X_{1-6}$ and Y are concerned.

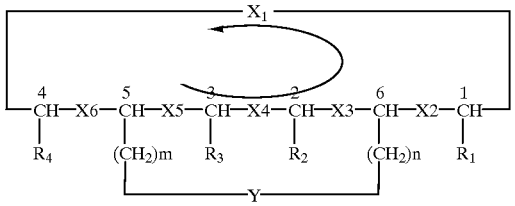

(Ia)

The groups $X_{1-6}$ and Y are in fact defined according to the aminoacid-sequence from the formal N- to the C-terminus of the peptide as they are represented in the linear structure, therefore reading Formula (Ia) no problem arises in the understanding of the linear structure as reported in the Examples.

As it can be seen, the compounds of formula (I) as described above present chiral centers: it is understood that this invention relates also to the several enantiomers.

More particularly the hydrophobic groups can be separately selected from the following:

a) groups $C_nH_{2n+1}$ wherein n=0, 1–4
b) linear- or branched alkyl groups corresponding to $C_nH_{2n}$-U-W wherein n=1–4; U=O, COO, CONH, S and W=alkyl-, aryl or alkylaryl-group containing from 1 to 15 carbon atoms
c) $(CH_2)_n$ —$C_6H_3$-A-B wherein n=0, 1–3; A and B, placed in any of the ortho, meta or para positions, same or different from one another, represent H, halogen, OR, NHR, $NR_2$, $CH_3$, SR wherein R is an alkyl-, aryl- or alkylaryl-group with less than 10 C atoms
d) $(CH_2)_n$ —$C_6H_{10}$ R', wherein n=0, 1–3 and R'=H, $C_{1-3}$ alkyl
e) $(CH_2)_n$-heterocycle, wherein n=0, 1–3 and for heterocycle it is meant: imidazolyl-2-yl, indolyl-3-yl, furanyl-3-yl, pyridyl-3-yl, imidazolyl-3-yl
f) a —$(CH_2)_s$— group, wherein s=3, 4, eventually OH-substituted or condensed with an aromatic group, which cyclizes with one of the two adjacent $X_{1-6}$ groups in order to produce the side chain of proline, hydroxyproline, octahydroindol-2-carboxylic acid, tetrahydroisoquinolinic acid
g) the side chain of a natural hydrophobic amino acid
h) the side chain of a natural hydrophilic amino acid, suitably substituted in order to render it hydrophobic
i) the side chain of non-natural hydrophobic amino acids selected from the group consisting of: norleucine, norvaline, alloisoleucine, cyclohexylglycine (Chg), α-amino-n-butyric acid (Aba), cyclohexylalanine (Cha), aminophenylbutyric acid (Pba), phenylalanines mono- and di- substituted in the ortho, meta and para positions of the benzene ring with one or more of the following groups: $C_{1-10}$ alkyl, $C_{1-10}$ alkoxy, halogen, β-2-thienylalanine, β-3-thienylalanine, β-2-furanylalanine, β-3-furanylalanine, β-2-piridylalanine, β-3-piridylalanine, β-4-piridylalanine, β(1-naphtyl) alanine, β-(2-naphtyl)alanine, O-alkylated serine-threonine- tyrosine-derivatives, S-alkyl cysteine, S-alkyl homocysteine, N-alkyl lysine, N-alkyl ornithine, N-alkyl 2,3 diaminopropionic acid.

More particularly, the side chain of a hydrophobic amino acid according to paragraph (g) is the side chain of an amino acid selected from the group consisting of: glycine, alanine, valine, isoleucine, methionine, phenylalanine, tyrosine, tryptophan, proline, histidine, aspargine, glutamine.

The side chain of a hydrophilic amino acid, suitably substituted in order to render it hydrophobic according to paragraph (h) is the chain of an amino acid selected from the group consisting of: serine, threonine, cysteine, aspartic acid, glutamic acid, t-carboxyglutamic acid, arginine, ornithine, lysine.

Preferably, the hydrophilic groups are selected from L-Q group, wherein L is a chemical bond or a linear or branched $C_{1-6}$-alkyl residue and Q is a hydrophilic group. Preferably Q is selected from the group consisting of: guanidine, amine, M, OM, —CO—NH—M, —NH—CO—M, an aromatic group which has been mono-, di- or tri-substituted in ortho, meta, para positions with M or OM groups, wherein M is a hydrophilic group.

With the term "hydrophilic group", for Q and M, it is preferably meant:

i) eventually substituted mono-, di-, tri-glycosidic residues;
ii) $C_{1-6}$ linear o cyclic alkyl chains comprising one or more polar groups;
iii) hydroxyl, amine, guanidine, carboxyl, sulfate, phosphonate, phosphate;
iv) residues bearing substituted hydrophilic groups which in biologic environment are hydrolysated, re-establishing the hydrophilic function.

As far as the definition according to paragraph (i) hereinabove is concerned, the following structures are preferably meant: hexoses or pentoses of the D or L series in α or β configuration, selected from the group wherein: all C atoms bear a free or protected hydroxylic group; one or more hydroxyls are substituted by: hydrogen, an amino or acylamino group; $C_6$ of hexoses and $C_5$ of pentoses are part of a carboxylic group; and wherein the eventually present 2 or 3 glycosidic units are linked by a glycosidic bond of α or β configuration.

Specific examples of glycosidic groups as defined above are: D or L ribose, D or L arabinose, D or L xylose, D or L lyxose, D or L allose, D or L altrose, D or L glucose, D or L mannose, D or L gulose, D or L idose, D or L galactose, D or L talose, D or L allulose, D or L fructose, D or L sorbose, D or L tagatose; 5-deoxy-D or L-arabinose, 2-deoxy-D or L-glucose, 2-deoxy-D or L-galactose, 2-deoxy-D or L-arabinose, 2-deoxy-D or L-ribose, D or L fucose, D or L ramnose; D-glucosamine, D-mannosamine, D-galactosamine, daunosamine, acosamine and N-acylate derivates thereof with lower fatty acids, i.e. having a N-formylic, acetylic, propionilic, butyric residue; glucuronic acid, galacturonic acid, cellobiose, lactose, maltose, D-lactosamine, cellotriose, maltotriose and protected derivates thereof.

The definition according to paragraph (ii) hereinabove applies to chains deriving from a polyol-residue, such as tris(hydroxymethyl)methyl, D or L arabitol, D or L erythrol, D or L galactytol, meso-inositol, D or L mannitol, D or L perseitol, D or L ribitol, D or L sorbitol, D or L xylitol; or those deriving from the residue of tartaric acid, glucaric acid, gluconic acid, bycine, quinic acid, mucic acid, glucosaminic acid.

Among the products of formula (I) as above indicated, the products wherein if one or both $R_1$ and $R_4$ groups are hydrophilic, both $R_2$ and $R_3$ groups are hydrophobic and viceversa, are particularly preferred. Compounds of formula (I) object of the present invention can be synthetized by the various techniques known in Literature, see e.g. M. Bodansky, "Peptide Chemistry", Springer-Verlag, 1988.

For example by means of in solution synthesis of the linear peptidic chain through subsequent coupling of suitably activated N-protected amino acids to an amino acid or to a C-protected peptidic chain, with isolation of the intermediates, subsequent selective de-protection of the C- and N-terminal chains, cyclization in polar organic solvents in diluted solution, hence selective de-protection of the side chains and at last cyclization of the same in polar organic solvents in diluted solution. The hydrophilic residue can be introduced both as protected amino acid derivative during the peptidic chain synthesis and by means of conjugation to the already formed peptide, as widely disclosed in Literature. Similarly a synthesis in solid phase of the peptidic chain from the C-terminal end to the N-terminal one on a insoluble polymeric support, the cyclization in solid phase between the previously de-protected side chains, the subsequent detachment from the polymeric support by means of hydrolysys in anhydrous hydrofluoric acid containing the suitable scavengers or in trifluoracetic acid containing the suitable scavengers or in aqueous bases and the cyclization of the monocyclic peptide in polar organic solvents in diluted solution, can be used for the preparation. The hydrophilic residue being introduced according to the above disclosed indications. According to a particular preparation method, the desired product can be obtained in solid phase using the 2-chlorotrytil resin (Barlos et al., Int. J. Peptide Protein Res., 37, 513–520, 1991) substituted with a protected amino acid having the Fmoc group at the N-terminal end; preferably the amino acid directly bond to the resin is the one having the $R_1$ or $R_3$ side chain. After the other amino acids being introduced in the sequence, the peptide is detached from the resin with diluted acetic acid and a first cyclization is performed between the free C-terminal and N-terminal end by means of the conventional classic synthesis methods. Subsequently, the amino acid side chains are de-protected in position 5 and 6, for example with trifluoracetic acid, and way is given to the second cyclization.

Other synthetic ways are anyway possible and largely described in Literature as above mentioned.

The compounds of formula (I) as above indicated have revealed to be powerful antagonists of the receptor $NK_2$ of the tachykinins, and hence may be administered in doses which are not higher than those required for the known products.

They can be therefore indicated for the treatment of arthritis, asthma, inflammations, tumoral growth, gastrointestinal hypermotility, Huntington's desease, neurites, neuralgia, hemicrania, hypertension, urinary incontinence, urticaria, symptoms from carcinoid desease, flu and colds.

The compounds of formula (I) object of the present invention are suitable for the parenteral, oral, inhalatory and sublingual administration for therapeutical purposes to the superior animals and to the humans, achieving pharmacological effects according to the above described features. For parenteral administrations (endovenous, intramuscular and intradermic) sterile solutions or lyophilized chemical preparations are used. For nasal, inhalatory and sublinqual administrations, according to the particular instance, aqueous solutions, aereosol preparations or capsules are used.

The doses of active principle in the above compositions can be comprised between 0.1 and 10 mg/kg of body weight.

EXAMPLE 1

Preparation of cyclo([Asn($\beta$-D-Glc)-Asp-Trp-Phe-Dap-Leu]cyclo(2$\beta$–5$\beta$)) (SEQ ID No. 1) compound of formula (I) wherein: Y=$X_1$=$X_2$=$X_3$=$X_4$=$X_5$=$X_6$=—CO—NH—; $R_1$=—$CH_2$—$CH(CH_3)_2$; $R_2$=—$CH_2$—$C_6H_5$, $R_3$=—$CH_2$indolyl-3-yl, $R_4$=—$CH_2$—CO—NH—($\beta$-D-Glc); m=n=1 and the carbon atoms $C_1$, $C_2$, $C_3$, $C_4$, $C_5$, $C_6$ have L configuration].

a) synthesis of the linear peptide H-Asn[($Ac_4$O)-$\beta$-D-Glc]-Asp(OtBu)-Trp-Phe-Dap(Boc)-Leu-OH.

1 g of 2-chlor trityl resin (1.6 mmol/g, Novabiochem) is functionalized with Fmoc-Leu-OH (0.6 eqs.) as described by Barlos et al., Int. J. Peptide Protein Res., 1991, 37, 513–520. The substitution degree of the resin is determined by dosing the group Fmoc, and it is equal to 0.364 meq/g. The subsequent 4 amino acids are coupled as free acids using an excess 3 of amino acid and HOBt (4 eqs.) and DCC (3 eqs.) as activators with reaction times of 1 hour. In the following order: Fmoc-Dap(Boc)-OH, Fmoc-Phe-OH, Fmoc-Trp-OH, Fmoc-Asp(OtBu)-OH are added. The last amino acid is coupled as Fmoc-Asn[($Ac_4$O)-$\beta$-D-Glc]-OPfp (Christiansen-Brams et al., J. Chem. Soc. Perkin Trans. I, 1993, 1461–1471), 2 eqs., with HOBt (2 eqs.) as activator, for 3 h.

After the de-protection of the group Fmoc, the detachment from the resin is performed, suspending it in 10 mL of a mixture of AcOH, TFE, DCM (1/1/8, v/v) at room temperature for 0.5 h. Thereafter the solvent is evaporated under vacuum at 30° C., it is again mixed with water and it is lyophilized. Yield in raw product: 405 mg (90%). Title HPLC: 70%. FAB-MS: $[M+H]^+$=1266; $t_r$: 14.7 min.

b) Synthesis of the bicyclic product cyclo([Asn(($Ac_4$O)-$\beta$-D-Glc)-Asp-Trp-Phe-Dap-Leu]cyclo(2$\beta$–5$\beta$)) (compound 2).

The linear raw product is cyclized in 1 mM solution in DMF, at 4° C., with 1 eq. of PyBOP and 1.2 eqs. of DIEA for 1 h. The mixture is dried and purified in HPLC obtaining 156 mg of the pure product (yield 39%). Title HPLC:>99%. FAB-MS: $[M+H]^+$=1248; $t_r$:18.4 min.

The monocyclic product is de-protected by solving it in 15 ml of TFA containing water at 10%. After 0.5 h, the mixture is diluted in water and it is lyophilized. The residue is dissolved in 1 mM solution in DMF, the solution is brought to 0° C. and 1 eq. of PyBOP and 1.2 eqs. of DIEA are added. After 5 h, it is dried and purified in HPLC. Yield 45% (70 mg). Title HPLC>99%. FAB-MS: $[M+H]^+$=1074; $t_r$:13.5 min.

c) Synthesis of the bicyclic product cyclo ([Asn($\beta$-D-Glc)-Asp-Trp-Phe-Dap-Leu]cyclo(2$\beta$–5$\beta$)).

70 mg of tetraacetylate product are dissolved in anhydrous methanol in 5 mM solution. The solution is brought to –20° C. and a 1 mM solution of sodium methylate in methanol is added to achieve pH=11. After 10' acetic acid is added to achieve neutral pH, high diluition with water and lyophilization follow. Yield 60%. Title HPLC: 98%. FAB-MS: $[M+H]^+$=906; $t_r$:9.3 min.

EXAMPLE 2

Preparation of cyclo([Ser($\beta$-D-Glc)-Asp-Trp-Phe-Dap-Leu]cyclo(2$\beta$–5$\beta$)) (SEQ ID No. 2) [compound of Formula (I) wherein: Y=$X_1$=$X_2$=$X_3$=$X_4$=$X_5$=$X_6$=—CO—NH—; $R_1$=—$CH_2$—$CH(CH_3)_2$; $R_2$=—$CH_2$—$C_6H_5$; $R_3$=—$CH_2$-indolyl-3-yl; $R_4$=—$CH_2$—O—($\beta$-D-Glc); m=n=1 and $C_1$, $C_2$, $C_3$, $C_4$, $C_5$, $C_6$ carbon atoms have L configuration.

a) synthesis of linear peptide H-Ser[($Bz_4$O)-$\beta$-D-Glc]-Asp(OtBu)-Trp-Phe-Dap(Boc)-Leu-OH.

The same procedure which has been used for Example 1), paragraph a), is utilized here till the addition of the last amino acid, which is coupled as Fmoc-Ser[($Bz_4$O)-$\beta$-D-Glc]-OPfp (obtained by the procedure which has been described by Vargas-Berenguel et al., J. Chem. Soc. Perkin Trans. I, 1994, 2615, 2619).

The detachment occurs as described above, in Example 1). Yield in raw product: 450 mg (83%). Title HPLC: 93%. FAB-MS: [M+H]⁺=1487; t$_r$:20.8 min.

b) Synthesis of bicyclic product cyclo([Ser[(Bz₄O)-β-D-Glc]-Asp-Trp-Phe-Dap-Leu]cyclo(2β–5β)).

The linear raw product is cyclized in 1 mM solution in DMF, at 4° C., with 1 eq. of PyBOP and 1.2 eqs. of DIEA for 1 h. The mixture is dried and purified in HPLC, obtaining 0.16 g of pure product (yield 35%). Title HPLC: >99%. FAB-MS: [M+H]⁺=1469; t$_r$:25.3 min.

The monocyclic product is de-protected by liquefying it in 10 mL of TFA containing water at 10%. After 0.5 h the mixture is diluted in water and it is lyophilized. The residue is dissolved in 1 mM solution in DMF, the solution is brought to 0° C. and 1 eq. of PyBOP and 1.2 eqs. of DIEA are added. After 24 h it is dried and purified in HPLC. Yield 63 mg (45%). Title HPLC: >99%. FAB-MS: [M+H]⁺=1295; t$_r$:21.6 min.

c) Synthesis of bicyclic product cyclo([Ser(β-D-Glc)-Asp-Trp-Phe-Dap-Leu]cyclo(2β–5β)).

20 mg of tetrabenzoylate product are dissolved in anhydrous methanol in 5 mM solution. The solution is brought to −20° C. and a 1 mM solution of sodium methylate in methanol is added to achieve pH=11. After 1.5 h acetic acid is added to achieve neutral pH, high dilution with water and lyophilization follow. Yield: 6.5 mg (48%). Title HPLC: >99%. FAB-MS: [M+H]⁺=878; t$_r$:9.6 min.

By similar procedures, the following compounds have been obtained:

EXAMPLE 3 cyclo([Asn(β-D-2-deoxy-2-amino-Glc)-Asp-Trp-Phe-Dap-Leu]cyclo(2β–5β)) (SEQ ID No. 3) [compound of Formula I) wherein R₄=—CH₂—CO—NH—(β-D-2-deoxy-2-amino-Glc) and the other substituents are as defined in Example 1].

EXAMPLE 4 cyclo ([Asn(β-D-2-deoxy-2-acetamido-Glc)-Asp-Trp-Phe-Dap-Leu]cyclo(2β–5β)) (SEQ ID No. 4) [compound of Formula I) wherein R₄=—CH₂—CO—NH—(β-D-2-deoxy-2-acetamido-Glc) and the other substituents are as defined in Example 1].

EXAMPLE 5 cyclo ([Nle-Asp-Trp-Phe-Dap-Asn(β-D-2-deoxy-2-acetamido-Glc]cyclo(2β–5β)) (SEQ ID No. 5) [compound of Formula I) wherein R₁=—CH₂—CO—NH—(β-D-2-deoxy-2-acetamido-Glc), R₄=—(CH₂)₃—CH₃] and the other substituents are as defined in Example 1].

EXAMPLE 6 cyclo([Asn(β-D-ribofuranosyl)-Asp-Trp-Phe-Dap-Leu] cyclo(2β–5β)) (SEQ ID No. 6) [compound of Formula I) wherein R₄=—CH₂—CO—NH—(β-D-ribofuranosyl) and the other substituents are as defined in Example 1].

EXAMPLE 7 cyclo([Ser(β-D-ribofuranosyl)-Asp-Trp-Phe-Dap-Leu] cyclo(2β–5β)) (SEQ ID No. 7) [compound of Formula I) wherein R₄=—CH₂—O—(β-D-ribofuranosyl), and the other substituents are as defined in Example 1].

EXAMPLE 8 cyclo ([Asn(β-L-arabinofuranosyl)-Asp-Trp-Phe-Dap-Leu]cyclo (2β–5β)) (SEQ ID No. 8) [compound of Formula I) wherein R₄=—CH₂—CO—NH—(β-L-arabinofuranosyl) and the other substituents are as defined in Example 1].

EXAMPLE 9 cyclo ([Ser(β-L-arabinofuranosyl)-Asp-Trp-Phe-Dap-Leu]cyclo (2β–5β)) (SEQ ID No. 9) [compound of Formula I) wherein R₄=—CH₂—O—(β-L-arabinofuranosyl) and the other substituents are as defined in Example 1].

EXAMPLE 10 cyclo([Asn(β-D-mannopyranosyl)-Asp-Trp-Phe-Dap-Leu]cyclo(2β–5β)) (SEQ ID 10) [compound of Formula I) wherein R₄=—CH₂—CO—NH—(β-D-mannopyranosyl) and the other substituents are as defined in Example 1].

EXAMPLE 11 cyclo([Ser(β-D-mannopyranosyl)-Asp-Trp-Phe-Dap-Leu]cyclo(2β–5β)) (SEQ ID No. 11) [compound of Formula I) wherein: R₄=—CH₂—O—(β-D-mannopiranosyl) and the other substituents are ad defined in Example 1].

EXAMPLE 12 cyclo ([Asn(β-D-galactopyranosyl)-Asp-Trp-Phe-Dap-Leu]cyclo (2β–5β)) (SEQ ID No. 12) [compound of Formula I) wherein R₄=—CH₂—CO—NH—(β-D-galactopyranosyl) and the other substituents are as defined in Example 1].

EXAMPLE 13 cyclo([Ser(β-D-galactopyranosyl)-Asp-Trp-Phe-Dap-Leu]cyclo(2β–5β) (SEQ ID No. 13) [compound of Formula I) wherein R₄=—CH₂—O—(β-D-galactopyranosyl) and the other substituents are as defined in Example 1].

EXAMPLE 14 cyclo ([Asn(β-D-glucuronopyranosyl)-Asp-Trp-Phe-Dap-Leu]cyclo (2β–5β)) (SEQ ID No. 14) [compound of Formula I) wherein R₄=—CH₂—CO—NH—(β-D-glucuronopyranosyl) and the other substituents are as defined in Example 1].

EXAMPLE 15 cyclo([Ser(β-D-glucuronopyranosyl)-Asp-Trp-Phe-Dap-Leu]cyclo (2β–5β)) (SEQ ID No. 15) [compound of Formula I) wherein R₄=—CH₂—O—(β-D-glucuronopyranosyl) and the other substituents are as defined in Example 1].

EXAMPLE 16 cyclo ([Asn(1-deoxy-sorbitol-1-yl)-Asp-Trp-Phe-Dap-Leu]cyclo (2β–5β)) (SEQ ID 16) [compound of Formula I) wherein R₄=—CH₂—CO—NH—(1-deoxy-sorbitol-1-yl) and the other substituents are as defined in Example 1].

EXAMPLE 17 cyclo ([Asn[4-O-(α-D-Glc)-β-D-Glc)]-Asp-Trp-Phe-Dap-Leu]cyclo-(2β–5β)) (SEQ ID No. 17) [compound of Formula I) wherein R₄=—CH₂—CO—NH—[4-O-(α-D-Glc)-β-D-Glc)] and the other substituents are as defined in Example 1].

EXAMPLE 18 cyclo([Asn[4-O-(α-D-galactopyranosyl)-β-D-Glc]-Asp-Trp-Phe-Dap-Leu]cyclo (2β–5β)) (SEQ ID No. 18)

[compound of Formula I) wherein $R_4$=—$CH_2$—CO—NH—[4-O(β-D-galactopyranosyl)-β-D-Glc)] and the other substituents are as defined in Example 1].

EXAMPLE 19 cyclo ([Asn[O-α-D-Glc-(1→4)-O-α-D-Glc-(1→4)-α-D-Glc]-Asp-Trp-Phe-Dap-Leu]cyclo(2β–5β)) (SEQ ID No. 19) [compound of Formula I) wherein: $R_4$=—$CH_2$—CO—NH—[O-α-D-Glc-(1→4)-O-α-D-Glc-(1→4)-α-D-Glc) and the other substituents are as defined in Example 1].

EXAMPLE 20 cyclo([Asn(D-2-deoxy-glucopyranos-2-yl)-Asp-Trp-Phe-Dap-Leu]cyclo (2β–5β)) (SEQ ID No. 20) [compound of Formula I) wherein $R_4$=—$CH_2$—CO—NH—(D-2-deoxy-gluco-pyranos-2-yl) and the other substituents are as defined in Example 1].

EXAMPLE 21 cyclo ([Dap[D(-)-quinyl]-Asp-Trp-Phe-Dap-Leu]cyclo (2β–5β)) (SEQ ID No. 21) [compound of Formula I) wherein: $R_4$=—$CH_2$—NH—[D(-)-quinyl], and the other substituents are as defined in Example 1].

EXAMPLE 22 cyclo ([Dap[D-gluconyl]-Asp-Trp-Phe-Dap-Leu]cyclo (2β–5β)) (SEQ ID No. 22) [compound of Formula I) wherein: $R_4$=—$CH_2$—NH—(D-gluconyl) and the other substituents are as defined in Example 1].

EXAMPLE 23 cyclo ([Dap[D-glucuryl]-Asp-Trp-Phe-Dap-Leu]cyclo (2β–5β)) (SEQ ID No. 23) [compound of Formula I) wherein $R_4$=—$CH_2$—NH—(D-glucuryl) and the other substituents are as defined in Example 1].

EXAMPLE 24 cyclo ([Dap(2-sulfo-benzoyl)-Asp-Trp-Phe-Dap-Leu] cyclo (2β–5β)) (SEQ ID No. 24) [compound of Formula I) wherein: $R_4$=—$CH_2$—NH—CO—$C_6H_4$—$SO_3H$ and the other substituents are as defined in Example 1].

EXAMPLE 25 cyclo ([Asn (4-sulfo-phenyl)-Asp-Trp-Phe-Dap-Leu] cyclo (2β–5β)) (SEQ ID No. 25) [compound of Formula I) wherein $R_4$=$CH_2$—CO—NH—$C_6H_4$—$SO_3H$ and the other substituents are as defined in Example 1].

EXAMPLE 26 cyclo([Asn(β-L-Glc)-Asp-Trp-Phe-Dap-Leu]cyclo (2β–5β)) (SEQ ID No. 26) [compound of Formula I) wherein $R_4$=—$CH_2$—CO—NH(β-L-Glc) and the other substituents are as defined in Example 1].

EXAMPLE 27 cyclo([Asn(β-D-2-deoxy-glucopyranos-2-yl)-Asp-Trp-Phe-Dap-Leu]cyclo(2β–5β)) (SEQ ID No. 27) [compound of formula I) wherein $R_4$=—$CH_2$—CO—NH—(D-2-deoxy-glucopyranos-2-yl) and the other substituents are as defined in Example 1].

EXAMPLE 28 cyclo ([Asn(D-2-deoxy-mannopyranos-2-yl)-Asp-Trp-Phe-Dap-Leu]-cyclo(2β–5β)) (SEQ ID No. 28) [compound of formula I) wherein $R_4$=—$CH_2$—CO—NH—(D-2-deoxy-mannopyranos-2-yl) and the other substituents are as defined in Example 1].

EXAMPLE 29 cyclo ([Asn(D-2-deoxy-galactopyranos-2-yl)-Asp-Trp-Phe-Dap-Leu]-cyclo(2β–5β)) (SEQ ID No. 29) [compound of formula I) wherein $R_4$=—$CH_2$—CO—NH—(D-2-deoxy-galactopyranos-2-yl) and the other substituents are as defined in Example 1].

EXAMPLE 30 cyclo ([Asn(β-D-xylopyranosyl)-Asp-Trp-Phe-Dap-Leu] cyclo(2β–5β)) (SEQ ID No. 30) [compound of formula I) wherein $R_4$=—$CH_2$—CO—NH—(β-D-xylo-pyranosyl) and the other substituents are as defined in Example 1].

EXAMPLE 31 cyclo ([Asn(3-sulfo-propionyl)-Asp-Trp-Phe-Dap-Leu] cyclo-(2β–5β)) (SEQ ID 31) [compound of formula I) wherein $R_4$=—$CH_2$—CO—NH—(3-sulfo-propionyl) and the other substituents are as defined in Example 1].

EXAMPLE 32 cyclo ([Dap(Lysyl)-Asp-Trp-Phe-Dap-Leu]cyclo (2β–5β)) (SEQ ID No. 32) [compound of formula I) wherein $R_4$=—$CH_2$—CO—NH—(Lysyl) and the other substituents are as defined in Example 1].

EXAMPLE 33 cyclo ([Dap(Arginyl)-Asp-Trp-Phe-Dap-Leu]cyclo (2β–5β)) (SEQ ID No. 33) [compound of formula I) wherein $R_4$=—$CH_2$—CO—NH—(Arginyl) and the other substituents are as defined in Example 1].

EXAMPLE 34 cyclo ([Dap(4-O-β-D-galactopyranosyl)-Asp-Trp-Phe-Dap-Leu]cyclo-(2β–5β)) (SEQ ID No. 34) [compound of formula I) wherein $R_4$=—$CH_2$—CO—NH—(4-O-β-D-galactopyranosyl) and the other substituents are as defined in Example 1].

EXAMPLE 35 cyclo ([Asn(2-deoxy-2-trifluoroacetamido-β-D-Glc)-Asp-Trp-Phe-Dap-Leu]cyclo(2β–5β)) (SEQ ID No. 35) [compound of formula I) wherein $R_4$=—$CH_2$—CO—NH—(2-deoxy-2-trifluoroacetamido-β-D-Glc) and the other substituents are as defined in Example 1].

Biological Activity

The capability of the compounds of the present invention to interact as agonists or antagonists with the neurokynin A (NKA) receptor has been valued in a in vitro test using the pulmonary artery of a rabbit (RPA) (Rovero et al., Neuropeptides, 1989, 13, 263–270) and their activity was determined as $pK_B$ (antilogarythm of the dissociation constant), as described in Jenkinson et al., TiPS, 12, 53–56, 1991. For example, compound 2 has shown a $pK_B$=8.67. The capability of the products of the present invention to interact as agonists or antagonists with NKA receptor has been valued in vivo as capability, after intravenous administration,to inhibit the agonist [betaAla[8]]NKA(4–10)-induced contractions of the urinary bladder in the anaesthetized mouse, as described in Maggi et al., J. Pharmacol. Exp. Ther., 1991, 257, 1172. Compound 1, e.g., causes, at dose of 10 nmol/Kg i.v., an inhibitory effect of 50–70%, as it has been valued at different times. The effect lasts over a period of more than 3 hours.

Abbreviations

Asn(β-D-Glc): $N^g$-(-D-glucopiranosyl)-L-asparagine

Asn[(Ac$_4$O)-β-D-Glc]: $N^g$-(2,3,4,6-tetra-O-acetyl-β-D-glucopiranosyl)-L-asparagine Fmoc-Asn[(Ac$_4$O)-β-D-Glc]-OPfp: $N^g$-(2,3,4,6-tetra-O-acetyl-β-D-glucopiranosyl)$N^a$-(fluoren-9-ylmethoxycarbonyl)-L-asparagine pentafluorophenyl esthere Ser(β-D-Glc): $O^g$-(β-D-glucopiranosyl)L-asparagine Ser[(Bz$_4$O)-β-D-Glc]: $O^g$-(2,3,4,6-tetra-O-benzoyl-β-D-glucopiranosyl)L-asparagine Fmoc-Ser[(Bz$_4$O)-β-D-Glc]-OPfp: $O^g$-(2,3,4,6-tetra-O-benzoyl-β-D-glucopiranosyl) $N^a$-(fluoren-9-ylmethoxycarbonyl)-L-serine pentafluorophenyl esther.

Glc: glucopyranosyl

---

What is claimed is:

1. Bicycl compounds of general Formula

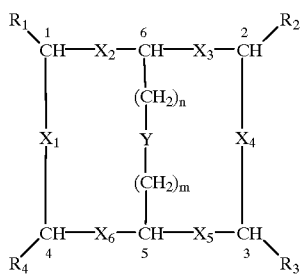

(I)

wherein $X_1$, $X_2$, $X_3$, $X_4$, $X_5$ and $X_6$, same or different from one another, represent a —NR'CO— or a —CONR'— group, where R' is H or $C_{1-3}$ alkyl;

Y represents a group selected from —NRCO—, —CONR— or —SS— wherein R is H or $C_{1-3}$ alkyl;

at least one of $R_1$, $R_2$, $R_3$ and $R_4$ groups, same or different from one another, is hydrophilic and the remaining groups are hydrophobic;

m and n, same or different from one another, are each an integer number from 1 to 4.

2. Compounds as claimed in claim 1, wherein the hydrophobic groups can be separately selected from the following:

a) groups corresponding to $C_nH_{2n+1}$ wherein n=0, 1–4;

b) linear or branched-alkyl groups corresponding to $C_nH_{2n}$-U-W wherein n=1–4; U=O, COO, CONH, S and W=alkyl-, aryl- or alkylaryl-group containing from 1 to 15 C atoms;

c) $(CH_2)_n$—$C_6H_3$-A-B wherein n=0, 1–3; A and B, placed in any of the ortho, meta, or para positions, same or different from one another, represent H, halogen, OR, NHR, $NR_2$, $CH_3$, SR wherein R is an alkyl-, aryl- or alkylaryl-group with less than 10 C atoms;

d) $(CH_2)_n$—$C_6H_{10}R'$, wherein n=0, 1–3 and R'=H, $C_{1-3}$ alkyl e) $(CH_2)_n$—heterocycle, wherein n=0, 1–3 and by the term heterocyclic imidazolyl-2-yl, indolyl-3-yl, furanyl-3-yl, piridyl-3-yl, imidazolyl-3-yl are meant;

f) a —$(CH_2)_s$— group wherein s=3, 4, eventually OH-substituted or condensed with an aromatic group, which cyclizes with one of the two adjacent $X_{1-6}$ groups in order to produce the side chain of proline, hydroxyproline, octahydroindol-2-carboxylic acid, tetrahydroisoquinolinic acid;

g) the side chain of a natural hydrophobic amino acid;

h) the side chain of a natural hydrophilic amino acid, suitably substituted in order to render it hydrophobic;

i) the side chain of non-natural hydrophobic amino acids selected from the group consisting of: norleucine, norvaline, alloisoleucine, ciclohexylglycine (Chg), alpha-amino-n-butyric-acid, (Aba), ciclohexylalanine (Cha), aminophenylbutyric acid (Pba), mono- and di-substituted phenylalonines in ortho, meta and para positions of the benzene ring with one or more of the following groups: $C_{1-10}$ alkyl, $C_{1-10}$ alkoxy, halogen, beta-2-thienylalanine, beta-3-thienylalanine, beta-2-furanylalanine, beta-3-furanylalanine, beta-2-piridylalanine, beta-3-piridylalanine, beta-4-piridylalanine, beta-(1-naphtyl)alanine, beta-(2-naphtyl)alanine, O-alkylated threonine, O-alkylated serine, O-alkylated tyrosine, S-alkyl cysteine, S-alkyl homocysteine, N-alkyl lysine, N-alkyl ornithine, N-alkyl 2,3 diaminopropionic acid.

3. Compounds as claimed in claim 2 wherein the side chain of a hydrophobic amino acid according to paragraph g) is the side chain of an amino acid selected from the group consisting of: glycine, alanine, valine, leucine, isoleucine, methionine, phenylalanine, tyrosine, tryptophan, proline, histidine, aspargine, glutamine.

4. Compounds as claimed in claim 2, wherein the side chain of an hydrophilic amino acid suitably substituted according to paragraph (h) is the side chain of an amino acid selected from the group consisting of: serine, threonine, cysteine, aspartic acid, glutamic acid, t-carboxyglutamic acid, arginine, ornythine, lysine.

5. Compounds according to claim 2 wherein the hydrophilic groups are chosen in the group L-Q wherein L is a chemical bond or a linear or branched $C_{1-6}$ alkyl-group and Q is chosen in the group consisting of:
  i) hydroxyl, amine, guanidine, carboxyl, sulfate, phosphonate, phosphate;
  ii) linear, branched or cyclic $C_{1-6}$ alkyl chain containing one or more hydroxyl, amine, guanidine, carboxyl, sulfate, phosphate;
  iii) an aromatic group mono-, di- or tri-substituted ortho-, meta-, para-position with hydroxyl, amino, guanidine, carboxyl, sulfate, phosphate;
  iv) a group M, OM, CONHM, NHCOM wherein M is an hydrophilic group
  v) an hydrophilic group according to points i)–iv) protected with groups which are biologically hydrolized reforming an hydrophilic group.

6. Compounds according to claim 5 wherein the group M is chosen in the group consisting of:
  i) eventually substituted mono-, di-, tri-glycosidic residues;
  ii) linear, branched or cyclic $C_{1-6}$ alkyl-chains, containing one or more groups hydroxyl, amine, guanidine, carboxyl, sulfate, phosphonate, phosphate.

7. Compounds of Formula (I) as claimed in claim 6, wherein the glycosidic residues are selected from the group consisting of:
  hexoses or pentoses of D or L series in α or β configuration, selected from the group wherein: all C atoms bear a free or protected hydroxylic group; one or more hydroxyls are substituted by: hydrogen; an amino or acylamino group; $C_6$ of hexoses and $C_5$ of pentoses are part of a carboxylic group; and wherein the eventually present 2 or 3 glycosidic units are linked by a glycosidic bond of α or β configuration.

8. Compounds of general Formula (I) according to claim 7 selected from the group consisting of: D or L ribose, D or L arabinose, D or L xylose, D or L lyxose, D or L allose, D or L altrose, D or L glucose, D or L mannose, D or L gulose, D or L idose, D or L galactose, D or L talose, D or L allulose, D or L fructose, D or L sorbose, D or L tagatose; 5-deoxy-D or L arabinose, 2-deoxy-D or L-glucose, 2-deoxy-D or L-galactose, 2-deoxy-D or L-arabinose, 2-deoxy-D or L-ribose, D or L fucose, D or L ramnose; D-glucosamine, D-mannosamine, D-galactosamine, daunosamine, acosamine and N-acylated derivatives of D-glucosamine, D-galactosamine, D-mannosamine, D-daunosamine, acosamine with lower fat acids, that is, containing a N-formylic, acetylic, propionilic, butyric residue; glucuronic acid, galacturonic acid; cellobiose, lactose, maltose, D-lactosamine, cellotriose, maltotriose; tris(hydroxymethyl) methyl, D or L arabitol, D or L erythrol, D or L perseitol, D or L ribitol, D or L sorbitol, D or L xylitol; or those from the residue of tartaric acid, glucaric acid, gluconic acid, bycine, quinic acid, mucic acid, glucosaminic acid.

9. Compounds of general Formula (I) according to claim 1, wherein if one or both $R_1$ and $R_4$ groups are hydrophilic, both $R_2$ and $R_3$ groups are hydrophobic or viceversa.

10. Compounds as claimed in claim 1, as hereinafter indicated:
  i) cyclo([Asn(β-D-Glc)-Asp-Trp-Phe-Dap-Leu]cyclo (2β–5β)) (SEQ ID No. 1)
  ii) cyclo([Ser(β-D-Glc)-Asp-Trp-Phe-Dap-Leu]cyclo (2β–5β)) (SEQ ID No. 2)
  iii) cyclo ([Asn(β-D-2-deoxy-2-amino-Glc)-Asp-Trp-Phe-Dap-Leu]cyclo (2β–5β)) (SEQ ID No. 3)
  iv) cyclo ([Asn(β-D-2-deoxy-2-acetamido-Glc)-Asp-Trp-Phe-Dap-Leu]cyclo(2β–5β)) (SEQ ID No. 4)
  v) cyclo([Nle-Asp-Trp-Phe-Dap-Asn(β-D-2-deoxy-2-acetamido-Glc)]cyclo(2β–5β)) (SEQ ID 5)
  vi) cyclo ([Asn(β-D-ribofuranosyl)-Asp-Trp-Phe-Dap-Leu]cyclo (2β–5β)) (SEQ ID 6)
  vii) cyclo ([Ser(β-D-ribofuranosyl)-Asp-Trp-Phe-Dap-Leu]cyclo (2β–5β)) (SEQ ID No. 7)
  viii) cyclo([Asn(β-L-arabinofuranosyl)-Asp-Trp-Phe-Dap-Leu]cyclo (2β–5β)) (SEQ ID No. 8)
  ix) cyclo([Ser(β-L-arabinofuranosyl)-Asp-Trp-Phe-Dap-Leu]cyclo (2β–5β)) (SEQ ID No. 9)
  x) cyclo([Asn(β-D-mannopyranosyl)-Asp-Trp-Phe-Dap-Leu]cyclo(2β–5β)) (SEQ ID No. 10)
  xi) cyclo([Ser(β-D-mannopyranosyl)-Asp-Trp-Phe-Dap-Leu]cyclo(2β–5β)) (SEQ ID No. 11)
  xii) cyclo([Asn(β-D-galactopyranosyl)-Asp-Trp-Phe-Dap-Leu]cyclo (2β–5β)) (SEQ ID No. 12)
  xiii) cyclo([Ser(β-D-galactopyranosyl)-Asp-Trp-Phe-Dap-Leu]cyclo (2β–5β)) (SEQ ID No. 13)
  xiv) cyclo ([Asn(β-D-glucuronopyranosyl)-Asp-Trp-Phe-Dap-Leu]cyclo(2β–5β)) (SEQ ID No. 14)
  xv) cyclo ([Ser(β-D-glucuronopyranosyl)-Asp-Trp-Phe-Dap-Leu]cyclo(2β–5β)) (SEQ ID No. 15)
  xvi) cyclo ([Asn(1-deoxy-sorbitol-1-yl)-Asp-Trp-Phe-Dap-Leu]cyclo (2β–5β)) (SEQ ID No. 16)
  xvii) cyclo ([Asn[(4-O-(α-D-Glc)-β-D-Glc)]-Asp-Trp-Phe-Dap-Leu]cyclo(2β–5β)) (SEQ ID No. 17)
  xviii) cyclo ([Asn[(4-O-(α-D-galactopyranosyl)-β-D-Glc)]-Asp-Trp-Phe-Dap-Leu]cyclo(2β–5β)) (SEQ ID No. 18)
  xix) cyclo ([Asn[O-α-D-Glc-(1→4)-O-α-D-Glc-(1→4)-α-D-Glc]-Asp-Trp-Phe-Dap-Leu]cyclo(2β–5β)) (SEQ ID No. 19)
  xx) cyclo ([Asn(D-2-deoxy-glucopyranos-2-yl)-Asp-Trp-Phe-Dap-Leu]cyclo(2β–5β)) (SEQ ID No. 20)
  xxi) cyclo ([Dap[D(−)-quinyl]-Asp-Trp-Phe-Dap-Leu] cyclo(2β–5β)) (SEQ ID No. 21)
  xxii) cyclo ([Dap[D-gluconyl]-Asp-Trp-Phe-Dap-Leu] cyclo (2β–5β)) (SEQ ID No. 22)
  xxiii) cyclo ([Dap[D-glucuryl]-Asp-Trp-Phe-Dap-Leu] cyclo(2β–5β)) (SEQ ID No. 23)
  xxiv) cyclo([Dap(2-sulfo-benzoyl)-Asp-Trp-Phe-Dap-Leu]cyclo(2β–5β)) (SEQ ID No. 24)
  xxv) cyclo ([Asn(4-sulfo-phenyl)-Asp-Trp-Phe-Dap-Leu] cyclo(2β–5β)) (SEQ ID No. 25)
  xxvi) cyclo ([Asn(β-L-Glc)-Asp-Trp-Phe-Dap-Leu]cyclo (2β–5β)) (SEQ ID No. 26)
  xxvii) cyclo ([Asn(β-D-2-deoxy-glucopyranos-2-yl)-Asp-Trp-Phe-Dap-Leu]cyclo(2β–5β)) (SEQ ID No. 27)
  xxviii) cyclo ([Asn(β-D-2-deoxy-mannopyranos-2-yl)-Asp-Trp-Phe-Dap-Leu]cyclo(2β–5β)) (SEQ ID No. 28)

xxix) cyclo ([Asn(D-2-deoxy-galactopyranos-2-yl)-Asp-Trp-Phe-Dap-Leu]cyclo(2β–5β)) (SEQ ID No. 29)

xxx) cyclo ([Asn(β-D-xylopyranosyl)-Asp-Trp-Phe-Dap-Leu]cyclo(2β–5β)) (SEQ ID No. 30)

xxxi) cyclo ([Asn(3-sulfo-propionyl)-Asp-Trp-Phe-Dap-Leu]cyclo (2β–5β)) (SEQ ID No. 31)

xxxii) cyclo ([Dap(Lysyl)-Asp-Trp-Phe-Dap-Leu]cyclo (2β–5β)) (SEQ ID No. 32)

xxxiii) cyclo ([Dap(Arginyl)-Asp-Trp-Phe-Dap-Leu] cyclo(2β–5β)) (SEQ ID No. 33)

xxxiv) cyclo ([Dap(4-O-β-D-galactopyranosyl)-Asp-Trp-Phe-Dap-Leu]cyclo(2β–5β)) (SEQ ID No. 34)

xxxv) cyclo ([Asn(2-deoxy-2-trifluoroacetamido-β-D-Glc)-Asp-Trp-Phe-Dap-Leu]cyclo(2β–5β)) (SEQ ID No. 35).

11. Pharmaceutical compositions containing as active principle compounds of general Formula (I) as claimed in claim 1, combined to suitable carriers.

12. Pharmaceutical compositions according to claim 11 for use as tachykinins antagonists.

13. Pharmaceutical compositions as claimed in claim 12 for treatment of arthrytis, asthma, inflammations, tumoral growth, gastrointestinal hypermotility, Huntington's disease, neuritis, neuralgia, hemicrania, hypertension, urinary incontinence, urticaria, symptoms from carcinoid syndrome, flu and cold.

14. Methods for treatment of arthrytis, asthma, inflammations, tumoral growth, gastrointestinal hypermotility, Huntington's disease, neuritis, neuralgia, hemicrania, hypertension, urinary incontinence, urticaria, symptoms from carcinoid syndrome, flu and cold, wherein doses comprised between 0.1 and 10 mg/Kg of body weight of active principle consisting of the products of Formula (I), according to claim 1, are administered to the patient.

* * * * *

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
      (A) LENGTH: 6 amino acids
      (B) TYPE: amino acid
      (C) STRANDEDNESS: single
      (D) TOPOLOGY: bicyclic (ii) MOLECULE TYPE: peptide (ix) FEATURE:
      (A) NAME/KEY: Modified-site
      (B) LOCATION: 5
      (D) OTHER INFORMATION: Xaa is Dap, i.e. diamino propionic (ix) FEATURE:
      (A) NAME/KEY: Modified-site
      (B) LOCATION: 1
      (D) OTHER INFORMATION: Asn is Asn(B-D-Glc), wherein Glc is glucopyranosyl (ix) FEATURE:
      (A) NAME/KEY: Modified-site
      (B) LOCATION: 1 and 6
      (D) OTHER INFORMATION: Asn and Leu are bound together to form a first cyclo (ix) FEATURE:
      (A) NAME/KEY: Modified-site
      (B) LOCATION: 2 and 5
      (D) OTHER INFORMATION: Asp and Dap are bound together to form a second cycl (xi) SEQUENCE DESCRIPTION: SEQ ID NO: 1:

Asn Asp Trp Phe Xaa Leu
1               5

(2) INFORMATION FOR SEQ ID NO: 2:

(i) SEQUENCE CHARACTERISTICS:
      (A) LENGTH: 6 amino acids
      (B) TYPE: amino acid
      (C) STRANDEDNESS: single
      (D) TOPOLOGY: bicyclic (ii) MOLECULE TYPE: peptide (ix) FEATURE:
      (A) NAME/KEY: Modified-site
      (B) LOCATION: 5
      (D) OTHER INFORMATION: Xaa is Dap, i.e. diamino propionic (ix) FEATURE:
      (A) NAME/KEY: Modified-site
      (B) LOCATION: 1

```
        (D) OTHER INFORMATION: Ser is Ser(B-D-Glc), wherein  Glc
            is glucopyranosyl (ix) FEATURE:
        (A) NAME/KEY: Modified-site
        (B) LOCATION: 1 and 6
        (D) OTHER INFORMATION: Ser and Leu are bound together to
            form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 2:

Ser Asp Trp Phe Xaa Leu
1               5

(2) INFORMATION FOR SEQ ID NO: 3:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1
        (D) OTHER INFORMATION: Asn  is  Asn(B-D-2-deoxy-2-amino-
            Glc), wherein Glc is glucopyranosyl (ix) FEATURE:
        (A) NAME/KEY: Modified-site
        (B) LOCATION: 1 and 6
        (D) OTHER INFORMATION: Asn and Leu are bound together to
            form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 3:

Asn Asp Trp Phe Xaa Leu
1               5

(2) INFORMATION FOR SEQ ID NO: 4:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1
        (D) OTHER INFORMATION: Asn is Asn(B-D-2-deoxy-2-acetamido-
```

```
            Glc), wherein Glc is glucopyranosyl (ix) FEATURE:
        (A) NAME/KEY: Modified-site
        (B) LOCATION: 1 and 6
        (D) OTHER INFORMATION: Asn and Leu are bound together to
            form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 4:

Asn Asp Trp Phe Xaa Leu
1               5

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Xaa is Nle, i.e. norleucine (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 6
        (D) OTHER INFORMATION: Asn is Asn(B-D-2-deoxy-2-acetamido
            -Glc), wherein Glc is glucopyranosyl (ix) FEATURE:
        (A) NAME/KEY: Modified-site
        (B) LOCATION: 1 and 6
        (D) OTHER INFORMATION: Nle and Asn are bound together to
            form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 5:

Xaa Asp Trp Phe Xaa Asn
1               5

(2) INFORMATION FOR SEQ ID NO: 6:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 5
        (D) OTHER INFORMATION: Xaa is Dap, i.e. diamino propionic
```

```
    (ix) FEATURE:
         (A) NAME/KEY: Modified-site
         (B) LOCATION: 1
         (D) OTHER INFORMATION: Asn is Asn(B-D-ribofuranosyl)

(ix) FEATURE:
         (A) NAME/KEY: Modified-site
         (B) LOCATION: 1 and 6
         (D) OTHER INFORMATION: Asn and Leu are bound together to
             form a first cyclo (ix) FEATURE:
         (A) NAME/KEY: Modified-site
         (B) LOCATION: 2 and 5
         (D) OTHER INFORMATION: Asp and Dap are bound together to
             form a second cyclo (xi) SEQUENCE DESCRIPTION: SEQ ID NO: 6:

Asn Asp Trp Phe Xaa Leu
1               5

(2) INFORMATION FOR SEQ ID NO: 7:

(i) SEQUENCE CHARACTERISTICS:
         (A) LENGTH: 6 amino acids
         (B) TYPE: amino acid
         (C) STRANDEDNESS: single
         (D) TOPOLOGY: bicyclic (ii) MOLECULE TYPE: peptide (ix) FEATURE:
         (A) NAME/KEY: Modified-site
         (B) LOCATION: 5
         (D) OTHER INFORMATION: Xaa is Dap, i.e. diamino propionic (ix) FEATURE:
         (A) NAME/KEY: Modified-site
         (B) LOCATION: 1
         (D) OTHER INFORMATION: Ser is Ser(B-D-ribofuranosyl)

(ix) FEATURE:
         (A) NAME/KEY: Modified-site
         (B) LOCATION: 1 and 6
         (D) OTHER INFORMATION: Ser and Leu are bound together to
             form a first cyclo (ix) FEATURE:
         (A) NAME/KEY: Modified-site
         (B) LOCATION: 2 and 5
         (D) OTHER INFORMATION: Asp and Dap are bound together to
             form a second cyclo (xi) SEQUENCE DESCRIPTION: SEQ ID NO: 7:

Ser Asp Trp Phe Xaa Leu
1               5

(2) INFORMATION FOR SEQ ID NO: 8:

(i) SEQUENCE CHARACTERISTICS:
         (A) LENGTH: 6 amino acids
         (B) TYPE: amino acid
         (C) STRANDEDNESS: single
         (D) TOPOLOGY: bicyclic (ii) MOLECULE TYPE: peptide (ix) FEATURE:
         (A) NAME/KEY: Modified-site
         (B) LOCATION: 5
         (D) OTHER INFORMATION: Xaa is Dap, i.e. diamino propionic (ix) FEATURE:
         (A) NAME/KEY: Modified-site
         (B) LOCATION: 1
```

```
            (D) OTHER INFORMATION: Asn is Asn(B-L-arabinofuranosyl)

(ix) FEATURE:
            (A) NAME/KEY: Modified-site
            (B) LOCATION: 1 and 6
            (D) OTHER INFORMATION: Asn and Leu are bound together to
                form a first cyclo (ix) FEATURE:
            (A) NAME/KEY: Modified-site
            (B) LOCATION: 2 and 5
            (D) OTHER INFORMATION: Asp and Dap are bound together to
                form a second cyclo (xi) SEQUENCE DESCRIPTION: SEQ ID NO: 8:

Asn Asp Trp Phe Xaa Leu
1               5

(2) INFORMATION FOR SEQ ID NO: 9:

(i) SEQUENCE CHARACTERISTICS:
            (A) LENGTH: 6 amino acids
            (B) TYPE: amino acid
            (C) STRANDEDNESS: single
            (D) TOPOLOGY: bicyclic (ii) MOLECULE TYPE: peptide (ix) FEATURE:
            (A) NAME/KEY: Modified-site
            (B) LOCATION: 5
            (D) OTHER INFORMATION: Xaa is Dap, i.e. diamino propionic (ix) FEATURE:
            (A) NAME/KEY: Modified-site
            (B) LOCATION: 1
            (D) OTHER INFORMATION: Ser is Ser(B-L-arabinofuranosyl)

(ix) FEATURE:
            (A) NAME/KEY: Modified-site
            (B) LOCATION: 1 and 6
            (D) OTHER INFORMATION: Ser and Leu are bound together to
                form a first cyclo (ix) FEATURE:
            (A) NAME/KEY: Modified-site
            (B) LOCATION: 2 and 5
            (D) OTHER INFORMATION: Asp and Dap are bound together to
                form a second cyclo (xi) SEQUENCE DESCRIPTION: SEQ ID NO: 9:

Ser Asp Trp Phe Xaa Leu
1               5

(2) INFORMATION FOR SEQ ID NO: 10:

(i) SEQUENCE CHARACTERISTICS:
            (A) LENGTH: 6 amino acids
            (B) TYPE: amino acid
            (C) STRANDEDNESS: single
            (D) TOPOLOGY: bicyclic (ii) MOLECULE TYPE: peptide (ix) FEATURE:
            (A) NAME/KEY: Modified-site
            (B) LOCATION: 5
            (D) OTHER INFORMATION: Xaa is Dap, i.e. diamino propionic (ix) FEATURE:
            (A) NAME/KEY: Modified-site
            (B) LOCATION: 1
            (D) OTHER INFORMATION: Asn is Asn(B-D-mannopyranosil)

(ix) FEATURE:
```

(A) NAME/KEY: Modified-site
                (B) LOCATION: 1 and 6
                (D) OTHER INFORMATION: Asn and Leu are bound together to
                    form a first cyclo (ix) FEATURE:
                (A) NAME/KEY: Modified-site
                (B) LOCATION: 2 and 5
                (D) OTHER INFORMATION: Asp and Dap are bound together to
                    form a second cyclo (xi) SEQUENCE DESCRIPTION: SEQ ID NO: 10:

Asn Asp Trp Phe Xaa Leu
1               5

(2) INFORMATION FOR SEQ ID NO: 11:

(i) SEQUENCE CHARACTERISTICS:
                (A) LENGTH: 6 amino acids
                (B) TYPE: amino acid
                (C) STRANDEDNESS: single
                (D) TOPOLOGY: bicyclic (ii) MOLECULE TYPE: peptide (ix) FEATURE:
                (A) NAME/KEY: Modified-site
                (B) LOCATION: 5
                (D) OTHER INFORMATION: Xaa is Dap, i.e. diamino propionic (ix) FEATURE:
                (A) NAME/KEY: Modified-site
                (B) LOCATION: 1
                (D) OTHER INFORMATION: Ser is Ser(B-D-mannopyranosyl)

(ix) FEATURE:
                (A) NAME/KEY: Modified-site
                (B) LOCATION: 1 and 6
                (D) OTHER INFORMATION: Ser and Leu are bound together to
                    form a first cyclo (ix) FEATURE:
                (A) NAME/KEY: Modified-site
                (B) LOCATION: 2 and 5
                (D) OTHER INFORMATION: Asp and Dap are bound together to
                    form a second cyclo (xi) SEQUENCE DESCRIPTION: SEQ ID NO: 11:

Ser Asp Trp Phe Xaa Leu
1               5

(2) INFORMATION FOR SEQ ID NO: 12:

(i) SEQUENCE CHARACTERISTICS:
                (A) LENGTH: 6 amino acids
                (B) TYPE: amino acid
                (C) STRANDEDNESS: single
                (D) TOPOLOGY: bicyclic (ii) MOLECULE TYPE: peptide (ix) FEATURE:
                (A) NAME/KEY: Modified-site
                (B) LOCATION: 5
                (D) OTHER INFORMATION: Xaa is Dap, i.e. diamino propionic (ix) FEATURE:
                (A) NAME/KEY: Modified-site
                (B) LOCATION: 1
                (D) OTHER INFORMATION: Asn is Asn(B-D-galactopyranosyl)

(ix) FEATURE:
                (A) NAME/KEY: Modified-site
                (B) LOCATION: 1 and 6
                (D) OTHER INFORMATION: Asn and Leu are bound together to

```
                  form a first cyclo (ix) FEATURE:
              (A) NAME/KEY: Modified-site
              (B) LOCATION: 2 and 5
              (D) OTHER INFORMATION: Asp and Dap are bound together to
                  form a second cyclo (xi) SEQUENCE DESCRIPTION: SEQ ID NO: 12:

Asn Asp Trp Phe Xaa Leu
1               5

(2) INFORMATION FOR SEQ ID NO: 13:

(i) SEQUENCE CHARACTERISTICS:
              (A) LENGTH: 6 amino acids
              (B) TYPE: amino acid
              (C) STRANDEDNESS: single
              (D) TOPOLOGY: bicyclic (ii) MOLECULE TYPE: peptide (ix) FEATURE:
              (A) NAME/KEY: Modified-site
              (B) LOCATION: 5
              (D) OTHER INFORMATION: Xaa is Dap, i.e. diamino propionic (ix) FEATURE:
              (A) NAME/KEY: Modified-site
              (B) LOCATION: 1
              (D) OTHER INFORMATION: Ser is Ser(B-D-galactopyranosyl)

(ix) FEATURE:
              (A) NAME/KEY: Modified-site
              (B) LOCATION: 1 and 6
              (D) OTHER INFORMATION: Ser and Leu are bound together to
                  form a first cyclo (ix) FEATURE:
              (A) NAME/KEY: Modified-site
              (B) LOCATION: 2 and 5
              (D) OTHER INFORMATION: Asp and Dap are bound together to
                  form a second cyclo (xi) SEQUENCE DESCRIPTION: SEQ ID NO: 13:

Ser Asp Trp Phe Xaa Leu
1               5

(2) INFORMATION FOR SEQ ID NO: 14:

(i) SEQUENCE CHARACTERISTICS:
              (A) LENGTH: 6 amino acids
              (B) TYPE: amino acid
              (C) STRANDEDNESS: single
              (D) TOPOLOGY: bicyclic (ii) MOLECULE TYPE: peptide (ix) FEATURE:
              (A) NAME/KEY: Modified-site
              (B) LOCATION: 5
              (D) OTHER INFORMATION: Xaa is Dap, i.e. diamino propionic (ix) FEATURE:
              (A) NAME/KEY: Modified-site
              (B) LOCATION: 1
              (D) OTHER INFORMATION: Asn is Asn(B-D-glucuronopyranosyl)

(ix) FEATURE:
              (A) NAME/KEY: Modified-site
              (B) LOCATION: 1 and 6
              (D) OTHER INFORMATION: Asn and Leu are bound together to
                  form a first cyclo (ix) FEATURE:
```

(A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 14:

Asn Asp Trp Phe Xaa Leu
1               5

(2) INFORMATION FOR SEQ ID NO: 15:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1
        (D) OTHER INFORMATION: Ser is Ser(B-D-glucuronopyranosyl)

(ix) FEATURE:
        (A) NAME/KEY: Modified-site
        (B) LOCATION: 1 and 6
        (D) OTHER INFORMATION: Ser and Leu are bound together to
            form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 15:

Ser Asp Trp Phe Xaa Leu
1               5

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1
        (D) OTHER INFORMATION: Asn is Asn(1-deoxy-sorbitol-1-yl)

(ix) FEATURE:
        (A) NAME/KEY: Modified-site
        (B) LOCATION: 1 and 6
        (D) OTHER INFORMATION: Asn and Leu are bound together to
            form a first cyclo (ix) FEATURE:
        (A) NAME/KEY: Modified-site
        (B) LOCATION: 2 and 5
        (D) OTHER INFORMATION: Asp and Dap are bound together to form a second cyclo (xi) SEQUENCE DESCRIPTION: SEQ ID NO: 16:

Asn Asp Trp Phe Xaa Leu
1               5

(2) INFORMATION FOR SEQ ID NO: 17:

(i) SEQUENCE CHARACTERISTICS:
                (A) LENGTH: 6 amino acids
                (B) TYPE: amino acid
                (C) STRANDEDNESS: single
                (D) TOPOLOGY: bicyclic (ii) MOLECULE TYPE: peptide (ix) FEATURE:
                (A) NAME/KEY: Modified-site
                (B) LOCATION: 5
                (D) OTHER INFORMATION: Xaa is Dap, i.e. diamino propionic (ix) FEATURE:
                (A) NAME/KEY: Modified-site
                (B) LOCATION: 1
                (D) OTHER INFORMATION: Asn is Asn[4-O-(a-D-Glc)-B-D-Glc],
                    wherein Glc is glucopyranosyl (ix) FEATURE:
                (A) NAME/KEY: Modified-site
                (B) LOCATION: 1 and 6
                (D) OTHER INFORMATION: Asn and Leu are bound together to
                    form a first cyclo (ix) FEATURE:
                (A) NAME/KEY: Modified-site
                (B) LOCATION: 2 and 5
                (D) OTHER INFORMATION: Asp and Dap are bound together to
                    form a second cyclo (xi) SEQUENCE DESCRIPTION: SEQ ID NO: 17:

Asn Asp Trp Phe Xaa Leu
1               5

(2) INFORMATION FOR SEQ ID NO: 18:

(i) SEQUENCE CHARACTERISTICS:
                (A) LENGTH: 6 amino acids
                (B) TYPE: amino acid
                (C) STRANDEDNESS: single
                (D) TOPOLOGY: bicyclic (ii) MOLECULE TYPE: peptide (ix) FEATURE:
                (A) NAME/KEY: Modified-site
                (B) LOCATION: 5
                (D) OTHER INFORMATION: Xaa is Dap, i.e. diamino propionic (ix) FEATURE:
                (A) NAME/KEY: Modified-site
                (B) LOCATION: 1
                (D) OTHER INFORMATION: Asn is
                    Asn[4-O-(B-D-galactopyranosyl)
                    -B-D-Glc]

(ix) FEATURE:
                (A) NAME/KEY: Modified-site
                (B) LOCATION: 1 and 6
                (D) OTHER INFORMATION: Asn and Leu are bound together to
                    form a first cyclo (ix) FEATURE:
                (A) NAME/KEY: Modified-site
                (B) LOCATION: 2 and 5
                (D) OTHER INFORMATION: Asp and Dap are bound together to form a second cyclo (xi) SEQUENCE DESCRIPTION: SEQ ID NO: 18:

Asn Asp Trp Phe Xaa Leu
1               5

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1
        (D) OTHER INFORMATION: Asn is Asn[O-a-D-Glc-(1>4)-O-a-D-
            Glc-(1>4)-a-D-Glc], wherein Glc is
            glucopyranosyl (ix) FEATURE:
        (A) NAME/KEY: Modified-site
        (B) LOCATION: 1 and 6
        (D) OTHER INFORMATION: Asn and Leu are bound together to
            form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 19:

Asn Asp Trp Phe Xaa Leu
1               5

(2) INFORMATION FOR SEQ ID NO: 20:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1
        (D) OTHER INFORMATION: Asn is Asn(D-2-deoxy-glucopyranos-
            2-yl)

(ix) FEATURE:
        (A) NAME/KEY: Modified-site
        (B) LOCATION: 1 and 6
        (D) OTHER INFORMATION: Asn and Leu are bound together to
            form a first cyclo (ix) FEATURE:
        (A) NAME/KEY: Modified-site
        (B) LOCATION: 2 and 5
        (D) OTHER INFORMATION: Asp and Dap are bound together to

```
              form a second cyclo (xi) SEQUENCE DESCRIPTION: SEQ ID NO: 20:

Asn Asp Trp Phe Xaa Leu
1               5

(2) INFORMATION FOR SEQ ID NO: 21:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Xaa is Dap[D(-)-quinyl]

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Dap[D(-)-quinyl] and Leu are bound
              together to form a first cyclo (ix) FEATURE:
        (A) NAME/KEY: Modified-site
        (B) LOCATION: 2 and 5
        (D) OTHER INFORMATION: Asp and Dap are bound together to
              form a second cyclo (xi) SEQUENCE DESCRIPTION: SEQ ID NO: 21:

Xaa Asp Trp Phe Xaa Leu
1               5

(2) INFORMATION FOR SEQ ID NO: 22:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Xaa is Dap[D-gluconyl]

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Dap[D-gluconyl] and Leu are bound
              together to form a first cyclo (ix) FEATURE:
        (A) NAME/KEY: Modified-site
        (B) LOCATION: 2 and 5
        (D) OTHER INFORMATION: Asp and Dap are bound together to
              form a second cyclo (xi) SEQUENCE DESCRIPTION: SEQ ID NO: 22:
```

```
Xaa Asp Trp Phe Xaa Leu
1               5

(2) INFORMATION FOR SEQ ID NO: 23:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Xaa is Dap[D-glucuryl]

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Dap[D-glucuryl] and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 23:

Xaa Asp Trp Phe Xaa Leu
1               5

(2) INFORMATION FOR SEQ ID NO: 24:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Xaa is Dap(sulfo-benzoyl)

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Dap(sulfo-benzoyl) and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 24:

Xaa Asp Trp Phe Xaa Leu
1               5
```

(2) INFORMATION FOR SEQ ID NO: 25:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Asn is Asn(4-sulfo-phenyl)

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Asn and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 25:

Asn Asp Trp Phe Xaa Leu
1               5

(2) INFORMATION FOR SEQ ID NO: 26:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Asn is Asn(B-L-Glc), wherein Glc is
            glucopyranosyl (ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Asn and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 26:

Asn Asp Trp Phe Xaa Leu
1               5

(2) INFORMATION FOR SEQ ID NO: 27:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Asn is Asn(B-D-2-deoxy-glucopyranos-
            2-yl)

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Asn and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 27:

Asn Asp Trp Phe Xaa Leu
1           5

(2) INFORMATION FOR SEQ ID NO: 28:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Asn is Asn(D-2-deoxy-mannopyranos-
            2-yl)

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Asn and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 28:

Asn Asp Trp Phe Xaa Leu
1           5

(2) INFORMATION FOR SEQ ID NO: 29:

```
        (i) SEQUENCE CHARACTERISTICS:
            (A) LENGTH: 6 amino acids
            (B) TYPE: amino acid
            (C) STRANDEDNESS: single
            (D) TOPOLOGY: bicyclic (ii) MOLECULE TYPE: peptide (ix) FEATURE:
            (A) NAME/KEY: Modified-site
            (B) LOCATION: 1
            (D) OTHER INFORMATION: Asn is
                Asn(D-2-deoxy-galactopyranos-
                2-yl (ix) FEATURE:
            (A) NAME/KEY: Modified-site
            (B) LOCATION: 5
            (D) OTHER INFORMATION: Xaa is Dap, i.e. diamino propionic (ix) FEATURE:
            (A) NAME/KEY: Modified-site
            (B) LOCATION: 1 and 6
            (D) OTHER INFORMATION: Asn and Leu are bound
                together to form a first cyclo (ix) FEATURE:
            (A) NAME/KEY: Modified-site
            (B) LOCATION: 2 and 5
            (D) OTHER INFORMATION: Asp and Dap are bound together to
                form a second cyclo (xi) SEQUENCE DESCRIPTION: SEQ ID NO: 29:

Asn Asp Trp Phe Xaa Leu
1               5

(2) INFORMATION FOR SEQ ID NO: 30:

(i) SEQUENCE CHARACTERISTICS:
            (A) LENGTH: 6 amino acids
            (B) TYPE: amino acid
            (C) STRANDEDNESS: single
            (D) TOPOLOGY: bicyclic (ii) MOLECULE TYPE: peptide (ix) FEATURE:
            (A) NAME/KEY: Modified-site
            (B) LOCATION: 1
            (D) OTHER INFORMATION: Asn is Asn(B-D-xylopyranosyl)

(ix) FEATURE:
            (A) NAME/KEY: Modified-site
            (B) LOCATION: 5
            (D) OTHER INFORMATION: Xaa is Dap, i.e. diamino propionic (ix) FEATURE:
            (A) NAME/KEY: Modified-site
            (B) LOCATION: 1 and 6
            (D) OTHER INFORMATION: Asn and Leu are bound
                together to form a first cyclo (ix) FEATURE:
            (A) NAME/KEY: Modified-site
            (B) LOCATION: 2 and 5
            (D) OTHER INFORMATION: Asp and Dap are bound together to
                form a second cyclo (xi) SEQUENCE DESCRIPTION: SEQ ID NO: 30:

Asn Asp Trp Phe Xaa Leu
1               5

(2) INFORMATION FOR SEQ ID NO: 31:
```

```
    (i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Asn is Asn(3-sulfo-propionyl)

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Asn and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 31:

Asn Asp Trp Phe Xaa Leu
1               5

(2) INFORMATION FOR SEQ ID NO: 32:

(i) SEQUENCE CHARACTERISTICS:
        (A) LENGTH: 6 amino acids
        (B) TYPE: amino acid
        (C) STRANDEDNESS: single
        (D) TOPOLOGY: bicyclic (ii) MOLECULE TYPE: peptide (ix) FEATURE:
        (A) NAME/KEY: Modified-site
        (B) LOCATION: 1
        (D) OTHER INFORMATION: Xaa is Dap(Lysyl)

(ix) FEATURE:
        (A) NAME/KEY: Modified-site
        (B) LOCATION: 5
        (D) OTHER INFORMATION: Xaa is Dap, i.e. diamino propionic (ix) FEATURE:
        (A) NAME/KEY: Modified-site
        (B) LOCATION: 1 and 6
        (D) OTHER INFORMATION: Dap(Lysyl) and Leu are bound
            together to form a first cyclo (ix) FEATURE:
        (A) NAME/KEY: Modified-site
        (B) LOCATION: 2 and 5
        (D) OTHER INFORMATION: Asp and Dap are bound together to
            form a second cyclo (xi) SEQUENCE DESCRIPTION: SEQ ID NO: 32:

Xaa Asp Trp Phe Xaa Leu
1               5

(2) INFORMATION FOR SEQ ID NO: 33:

(i) SEQUENCE CHARACTERISTICS:
        (A) LENGTH: 6 amino acids
        (B) TYPE: amino acid
```

(C) STRANDEDNESS: single
            (D) TOPOLOGY: bicyclic (ii) MOLECULE TYPE: peptide (ix) FEATURE:
            (A) NAME/KEY: Modified-site
            (B) LOCATION: 1
            (D) OTHER INFORMATION: Xaa is Dap(Arginyl)

(ix) FEATURE:
            (A) NAME/KEY: Modified-site
            (B) LOCATION: 5
            (D) OTHER INFORMATION: Xaa is Dap, i.e. diamino propionic (ix) FEATURE:
            (A) NAME/KEY: Modified-site
            (B) LOCATION: 1 and 6
            (D) OTHER INFORMATION: Dap(Arginyl) and Leu are bound
                together to form a first cyclo (ix) FEATURE:
            (A) NAME/KEY: Modified-site
            (B) LOCATION: 2 and 5
            (D) OTHER INFORMATION: Asp and Dap are bound together to
                form a second cyclo (xi) SEQUENCE DESCRIPTION: SEQ ID NO: 33:

Xaa Asp Trp Phe Xaa Leu
1               5

(2) INFORMATION FOR SEQ ID NO: 34:

(i) SEQUENCE CHARACTERISTICS:
            (A) LENGTH: 6 amino acids
            (B) TYPE: amino acid
            (C) STRANDEDNESS: single
            (D) TOPOLOGY: bicyclic (ii) MOLECULE TYPE: peptide (ix) FEATURE:
            (A) NAME/KEY: Modified-site
            (B) LOCATION: 1
            (D) OTHER INFORMATION: Xaa is Dap(4-O-B-D-galactopyranosyl)

(ix) FEATURE:
            (A) NAME/KEY: Modified-site
            (B) LOCATION: 5
            (D) OTHER INFORMATION: Xaa is Dap, i.e. diamino propionic (ix) FEATURE:
            (A) NAME/KEY: Modified-site
            (B) LOCATION: 1 and 6
            (D) OTHER INFORMATION: Dap(4-O-B-D-galactopyranosyl) and
                Leu
                are bound together to form a first
                cyclo (ix) FEATURE:
            (A) NAME/KEY: Modified-site
            (B) LOCATION: 2 and 5
            (D) OTHER INFORMATION: Asp and Dap are bound together to
                form a second cyclo (xi) SEQUENCE DESCRIPTION: SEQ ID NO: 34:

Xaa Asp Trp Phe Xaa Leu
1               5

(2) INFORMATION FOR SEQ ID NO: 35:

(i) SEQUENCE CHARACTERISTICS:
            (A) LENGTH: 6 amino acids
            (B) TYPE: amino acid
            (C) STRANDEDNESS: single -continued

```
          (D) TOPOLOGY: bicyclic (ii) MOLECULE TYPE: peptide (ix) FEATURE:
          (A) NAME/KEY: Modified-site
          (B) LOCATION: 1
          (D) OTHER INFORMATION: Asn is Asn(2-deoxy-2-trifluoro-
              acetoamido-B-D-Glc, wherein Glc is
              glucopyranosyl (ix) FEATURE:
          (A) NAME/KEY: Modified-site
          (B) LOCATION: 5
          (D) OTHER INFORMATION: Xaa is Dap, i.e. diamino propionic (ix) FEATURE:
          (A) NAME/KEY: Modified-site
          (B) LOCATION: 1 and 6
          (D) OTHER INFORMATION: Asn and Leu are bound
              together to form a first cyclo (ix) FEATURE:
          (A) NAME/KEY: Modified-site
          (B) LOCATION: 2 and 5
          (D) OTHER INFORMATION: Asp and Dap are bound together to
              form a second cyclo (xi) SEQUENCE DESCRIPTION: SEQ ID NO: 35:

Xaa Asp Trp Phe Xaa Leu
1               5
```